(12) United States Patent
Powers et al.

(10) Patent No.: US 9,674,026 B1
(45) Date of Patent: Jun. 6, 2017

(54) BEAM POSITION MONITOR FOR ENERGY RECOVERED LINAC BEAMS

(71) Applicant: JEFFERSON SCIENCE ASSOCIATES, LLC, Newport News, VA (US)

(72) Inventors: Thomas Powers, Poquoson, VA (US); Pavel Evtushenko, Yorktown, VA (US)

(73) Assignee: JEFFERSON SCIENCE ASSOCIATES, LLC, Newport News, VA (US)

( * ) Notice: Subject to any disclaimer, the term of this patent is extended or adjusted under 35 U.S.C. 154(b) by 0 days.

(21) Appl. No.: 15/165,498

(22) Filed: May 26, 2016

(51) Int. Cl.
*H04L 27/00* (2006.01)
*H04L 27/38* (2006.01)
*A61N 5/10* (2006.01)

(52) U.S. Cl.
CPC ........ *H04L 27/3827* (2013.01); *A61N 5/1049* (2013.01); *A61N 5/1069* (2013.01); *A61N 5/1077* (2013.01)

(58) Field of Classification Search
CPC .......... H05H 7/22; H05H 7/00; H05H 1/0081; G01T 1/29
USPC ......................................................... 375/261
See application file for complete search history.

(56) References Cited

U.S. PATENT DOCUMENTS

| | | | | |
|---|---|---|---|---|
| 2,057,766 A * | 10/1936 | Brubaker | ............. | C09D 167/08 106/252 |
| 2,545,595 A * | 3/1951 | Alvarez | ................... | H05H 9/00 220/2.3 R |
| 3,115,467 A * | 12/1963 | Bolt | .......................... | C10M 1/08 376/306 |
| 3,133,227 A * | 5/1964 | Nunan | ....................... | H01J 3/02 250/281 |
| 3,218,562 A * | 11/1965 | Serduke | ................... | H05H 5/06 313/62 |
| 4,062,012 A * | 12/1977 | Colbert | ................. | G01S 7/2922 342/90 |
| 5,057,766 A * | 10/1991 | Nakata | ..................... | H05H 7/00 324/452 |
| 5,459,393 A * | 10/1995 | Tanaka | ..................... | G01T 1/29 315/500 |
| 7,102,144 B2 * | 9/2006 | Matsuda | .................. | A61N 5/10 250/492.1 |
| 7,279,882 B1 * | 10/2007 | Degtiarenko | .......... | G01N 23/06 250/397 |
| 7,382,861 B2 * | 6/2008 | Madey | ..................... | H05G 2/00 378/119 |
| 8,072,255 B2 * | 12/2011 | Cicalini | ............... | H03D 7/1441 327/113 |

(Continued)

FOREIGN PATENT DOCUMENTS

DE    WO 2011015609 A2 *    2/2011    ............... H05H 7/22

*Primary Examiner* — Daniel Washburn
*Assistant Examiner* — Berhanu Tadese

(57) ABSTRACT

A method of determining the beam position in an energy recovered linac (ERL). The method makes use of in phase and quadrature (I/Q) demodulation techniques to separate the pickup signal generated by the electromagnetic fields generated by the first and second pass beam in the energy recovered linac. The method includes using analog or digital based I/Q demodulation techniques in order to measure the relative amplitude of the signals from a position sensitive beam pickup such as a button, strip line or microstripline beam position monitor.

2 Claims, 1 Drawing Sheet

(56) References Cited

U.S. PATENT DOCUMENTS

| | | | | |
|---|---|---|---|---|
| 8,093,840 B1* | 1/2012 | Douglas | ............... | H05H 7/08 |
| | | | | 315/505 |
| 8,130,045 B1* | 3/2012 | Allison | ............... | H03L 7/081 |
| | | | | 250/396 R |
| 2007/0115071 A1* | 5/2007 | Barov | ............... | H05H 7/22 |
| | | | | 331/79 |
| 2013/0113503 A1* | 5/2013 | Ruf | ............... | G01T 1/29 |
| | | | | 324/654 |

* cited by examiner

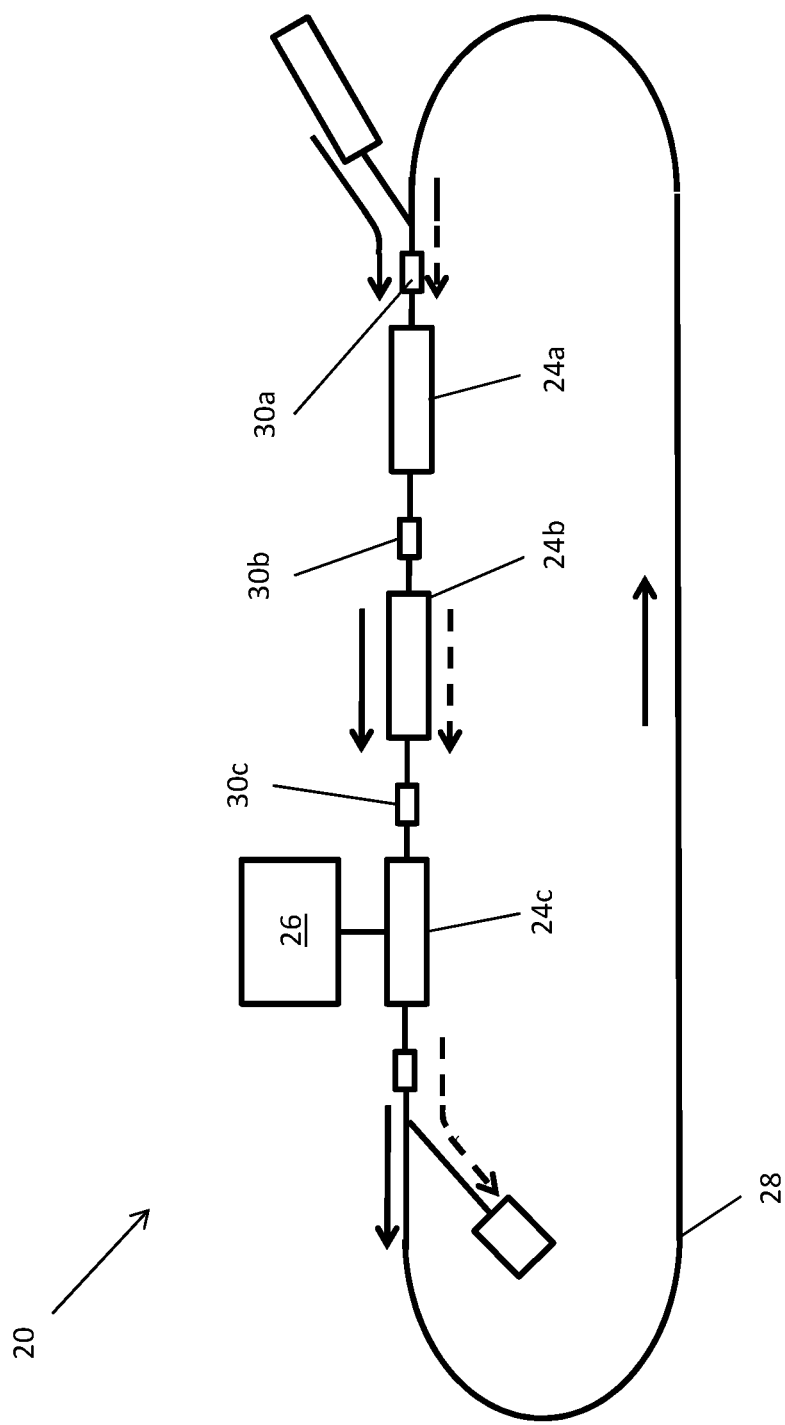

BEAM POSITION MONITOR FOR ENERGY RECOVERED LINAC BEAMS

GOVERNMENT LICENSE RIGHTS STATEMENT

This invention was made with government support under Management and Operating Contract No. DE-AC05-06OR23177 awarded by the Department of Energy. The United States Government has certain rights in the invention.

FIELD OF THE INVENTION

The present invention relates to beam position monitors used in particle accelerators and beamlines and more particularly to a method for analog or digital based I/Q demodulation techniques in order to measure the relative amplitude of the signals from a position sensitive beam pickup such as a button, strip line or microstripline beam position monitor.

BACKGROUND

Although various non-intercepting electromagnetic beam position monitors have been developed for use in particle accelerators and beamlines, the cost of the signal processing to recover the beam position information can be substantially high. This is especially the case when the currents associated with periodically spaced beam bunches are considered in the time domain. As a result of requiring Giga-bit sampling acquisition hardware, time domain processing is very expensive.

Accordingly, what is needed is an accurate, reliable, and low cost option for beam position monitoring in an energy recovered linac.

OBJECT OF THE INVENTION

The object of the present invention is to provide a lower cost method for monitoring the beam position in an energy recovered linac.

SUMMARY OF THE INVENTION

The present invention method of determining the beam position in an energy recovered linac. The method makes use of in phase and quadrature (I/Q) demodulation techniques to separate out the first and second pass beam in the energy recovered linac. The method includes using analog or digital based I/Q demodulation techniques in order to measure the relative amplitude of the signals from a position sensitive beam pickup such as a button, strip line or microstripline beam position monitor.

BRIEF DESCRIPTION OF THE SEVERAL VIEWS OF THE DRAWING(S)

Reference is made herein to the accompanying drawings, which are not necessarily drawn to scale, and wherein:

FIG. 1 is a layout view of an accelerator that makes use of an energy recovered linac (ERL) in accordance with embodiments of the invention.

DETAILED DESCRIPTION

This invention is for a novel technique which makes use of in phase and quadrature (I/Q) demodulation techniques to separate out first and second pass beam in an energy recovered linac. The system will make use of either analog or digital based I/Q demodulation techniques in order to measure the relative amplitude of the signals from a position sensitive beam pickup such as a button, strip line or microstripline beam position monitor.

With reference to FIG. 1 there is shown an energy recovered linac 20 with a a plurality of RF cavities 24a, 24b, and 24c supplied by RF energy from an RF system 26 that accelerates particles around a path 28. The energy recovery linac 20 is an accelerator topology where the first pass beam extracts energy from the RF cavities 24a, 24b, and 24c and the second pass beam deposits an approximately equal amount of energy into the RF cavities. Thus the net energy from the RF system 26 that is deposited in the vector sum of the beams is very small as compared to the energy that is deposited into the first pass beam. In order to get good energy recovery the second pass beam must be close to 180° out of phase with the first pass beam, where the phase is referenced to the electromagnetic field inside the RF cavity which is operated at a frequency of $f_C$. The bunch repetition frequency, $f_0$, is the rate at which electron bunches pass a location in the accelerator. It can be the same frequency as the cavity frequency. It can also be a sub harmonic of the cavity frequency. Here a sub-harmonic is defined as $f_0=f_C/m$ where m is an integer value greater than 1. FIG. 1 further illustrates three potential locations in which a beam position monitor can be placed on an ERL, including a first beam position monitor 30a upstream of RF cavity 24a, a second beam position monitor 30b between RF cavities 24a and 24b, and a third beam position monitor 30c between cavities 24b and 24c.

The bunch length, measured in time, is generally much shorter than the period of the RF. Although the examples in this description describe the beam as having Gaussian temporal characteristics, any beam pulse which has a bunch length short relative to the period of the RF frequency can be treated in a similar manner. Additionally, there are several different detector configurations which generate RF signals that can be processed in the same manner. As such this invention applies to all of the various detector configurations.

The following is an example of mathematical background for one such sensor, a button position monitor (BPM). Other similar treatment for other types of sensor will yield the same fundamental results. The voltage on a button BPM, $V_B$, with a charge Q is given by a doublet pulse of the form:

$$V_B = \frac{-KQt}{\sigma^3} e^{\frac{-t^2}{2\sigma^2}}$$

Here K is a geometric constant that is based on the size, shape and position of the button within a vacuum chamber; Q is the bunch charge, σ is the rms bunch length. If the bunches are repeated at a frequency of $\omega_0=2\pi f_0$ one can show that the beam can be represented by a Taylor series expansion of:

$$V_{B\_Accelerated}(t) = \langle I_B \rangle K \sum_{m=1}^{\infty} m^2 \omega_0 \sigma^2 e^{\left(\frac{-m^2\omega_0^2\sigma^2}{2}\right)} \cos(m\omega_0 t)$$

For perfect energy recovery one has to change the phase of the decelerated beam by 180° in the cavity phase or:

$$T_{Delay} = \frac{1}{2f_c}$$

Applying the same transform one would obtain the following in the Taylor series expansion.

$$V_{B\_Decelerated}(t) = \langle I_B \rangle - 2\langle I_B \rangle K \sum_{m=1}^{\infty} m^2 \omega_0 \sigma^2 e^{\left(\frac{-m^2\omega_0^2\sigma^2}{2}\right)} \cos\left(m\omega_o t + \frac{m\omega_0}{2f_c}\right)$$

When the RF frequency, ($m\omega_0$), of the Beam Position monitor receiver is chosen such that $$\frac{m\omega_0}{2f_c} = k\pi + \frac{\pi}{2} \text{ Where } m = 1, 2, 3, 4 \ldots \text{ and } k = 0, 1, 2, \ldots$$

$$\frac{m\pi f_0}{f_c} = k\pi + \frac{\pi}{2}$$

$$\frac{mf_0}{f_c} = k + \frac{1}{2}$$

or $$\frac{mf_0}{f_c} = k + \frac{1}{2}$$

The decelerated beam will be ±90° out of phase with the accelerated beam and I/Q methods could be used to distinguish between the two signals. For example for uniformly spaced beam bunches at $f_0$=100 MHz and a cavity frequency and $f_C$=1000 MHz leads to:

$$\frac{m}{10} = k + \frac{1}{2} \rightarrow m = 10k + 5$$

Thus a receiver frequency or one of the following 0.5 GHz, 1.5 GHz, 2.5 GHz . . . . , will provide a signal for accelerated beam that is +90° or −90° out of phase with the decelerated beam.

I/Q receivers are capable of separating such signals with a high level of fidelity. They have been implemented using a number of signal processing techniques, such as RF, base band, synchronous I/Q analog to digital receivers, and direct digital down converters. Forms of all of these approaches are available as commercial products. Thus if one were to introduce just an accelerated beam into the linac and adjust the relative phase between an RF reference and the receiver, using either analog or digital techniques, until the Q-channel has zero amplitude then that channel of the position monitor would be synchronized for use. One can then apply both accelerated and decelerated beam to the system. The I-channels would contain the position information for the accelerated beam and the Q-channels would contain the position information for the decelerated beam. If perfect energy recovery does not take place one would introduce a correction based on the accelerated/decelerated beam cavity phase difference from 180°, which could be corrected based on the phase difference.

Although this approach will not work for CW beams that have a bunch repetition frequency $f_0=f_C$, if there are gaps in the bunch pattern, which introduce harmonics such that there is frequency content in the detected signals at $f_X=Yf_C$ where Y=0.5, 1.5, 2.5, . . . then the method of the present invention will again apply and would provide a means for separating out accelerated and decelerated beam positions.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment herein was chosen and described in order to best explain the principles of the invention and the practical application, and to enable others of ordinary skill in the art to understand the invention for various embodiments with various modifications as are suited to the particular use contemplated.

What is claimed is:

1. A method for measuring the relative amplitude of the signals from a position sensitive beam pickup in an energy recovered linear accelerator, comprising:
    providing an in phase and quadrature (I/O) beam position monitor receiver including I-channels and Q-channels;
    introducing an accelerated beam into the energy recovered linear accelerator;
    selecting an RF reference;
    adjusting the relative phase between the RF reference and the I/O receiver until the Q-channel has zero amplitude to synchronize the Q-channel of the position monitor for use;
    applying an accelerated beam and a decelerated beam to the system wherein the phase of the decelerated beam, relative to that of the electromagnetic fields within the accelerating cavity, is that of the accelerating beam plus or minus approximately 180°;
    setting the RF frequency ($m\omega_0$) of the beam position monitor receiver to a harmonic of the RF cavity frequency, where m is a whole integer 1, 2, 3, 4 . . . and $\omega_0$=2π$f_0$, where $f_0$ is the bunch repetition frequency, with the additional condition that $m\omega_0=k\omega_c$, where k is 0.5, 1.5, 2.5, . . . , $\omega_c$=2π$f_c$, and $f_c$ is the energy recovered linear accelerator cavity frequency;
    reading the position information for the accelerated beam from the I-channels;
    reading the position information for the decelerated beam from the Q-channels;
    determining a cavity phase difference between the accelerated beam and the decelerated beam to determine if the energy recovered linear accelerator is at maximum energy recovery; and
    introducing a correction based on the accelerated/decelerated beam cavity phase difference from 180° in order to improve the accuracy of the beam position calculation.

2. The method of claim 1 further comprising:
    the RF frequency ($m\omega_0$) of the beam position monitor receiver is set to one of the following harmonics of the RF cavity frequency 0.5, 1.5, 2.5, 3.5 . . . n.5, where n is a whole integer to provide a signal for the accelerated beam that is +90° or −90° out of phase with the decelerated beam.

* * * * *